United States Patent
Kim et al.

(10) Patent No.: US 12,113,173 B2
(45) Date of Patent: Oct. 8, 2024

(54) NON-AQUEOUS ELECTROLYTE INCLUDING ADDITIVE FOR NON-AQUEOUS ELECTROLYTE AND LITHIUM SECONDARY BATTERY INCLUDING THE SAME

(71) Applicant: LG Energy Solution, Ltd., Seoul (KR)

(72) Inventors: Hyung Tae Kim, Daejeon (KR); Chul Haeng Lee, Daejeon (KR); Jeong Woo Oh, Daejeon (KR); Byung Chun Park, Daejeon (KR); Young Mi Seo, Daejeon (KR); Sung Guk Park, Daejeon (KR)

(73) Assignee: LG Energy Solution, Ltd., Seoul (KR)

( * ) Notice: Subject to any disclaimer, the term of this patent is extended or adjusted under 35 U.S.C. 154(b) by 0 days.

(21) Appl. No.: 18/574,964

(22) PCT Filed: Sep. 29, 2022

(86) PCT No.: PCT/KR2022/014692
§ 371 (c)(1),
(2) Date: Dec. 28, 2023

(87) PCT Pub. No.: WO2023/055144
PCT Pub. Date: Apr. 6, 2023

(65) Prior Publication Data
US 2024/0274882 A1    Aug. 15, 2024

(30) Foreign Application Priority Data
Sep. 30, 2021 (KR) .................. 10-2021-0129872

(51) Int. Cl.
| | |
|---|---|
| *H01M 10/0567* | (2010.01) |
| *C07D 207/335* | (2006.01) |
| *H01M 10/0525* | (2010.01) |
| *H01M 10/0568* | (2010.01) |

(52) U.S. Cl.
CPC .... *H01M 10/0567* (2013.01); *C07D 207/335* (2013.01); *H01M 10/0525* (2013.01); *H01M 10/0568* (2013.01); *H01M 2300/0037* (2013.01)

(58) Field of Classification Search
None
See application file for complete search history.

(56) References Cited

U.S. PATENT DOCUMENTS

| | | |
|---|---|---|
| 5,522,981 A | 6/1996 | Lacaze et al. |
| 9,627,712 B2 * | 4/2017 | Cheng ............... H01M 10/0568 |
| 2012/0077076 A1 | 3/2012 | Cheng et al. |
| 2012/0171576 A1 | 7/2012 | Tsai et al. |
| 2012/0171579 A1 | 7/2012 | Tsai et al. |
| 2012/0237836 A1 | 9/2012 | Kim |
| 2014/0212746 A1 | 7/2014 | Kim |
| 2014/0220417 A1 | 8/2014 | Cheng et al. |
| 2015/0229003 A1 | 8/2015 | Lim et al. |
| 2019/0207257 A1 | 7/2019 | Hiasa et al. |

FOREIGN PATENT DOCUMENTS

| | | |
|---|---|---|
| CN | 102569886 A | 7/2012 |
| CN | 112563571 A | 3/2021 |
| JP | H07331491 A | 12/1995 |
| JP | 2013-020701 A | 1/2013 |
| JP | 2016001567 A | 1/2016 |
| JP | 2018041588 A | 3/2018 |
| KR | 20120104930 A | 9/2012 |
| KR | 20140095901 A | 8/2014 |
| KR | 20150094088 A | 8/2015 |

OTHER PUBLICATIONS

International Search Report for PCT/KR2022/014692 mailed Dec. 27, 2022. 3 pages.
Extended European Search Report including Written Opinion for Application No. 22876916.2 dated Sep. 2, 2024. 8 pgs.

\* cited by examiner

*Primary Examiner* — Wyatt P McConnell
(74) *Attorney, Agent, or Firm* — Lerner David LLP

(57) ABSTRACT

A non-aqueous electrolyte including an additive represented by Formula 1 is described:

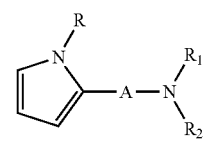

[Formula 1]

wherein in Formula 1, R may be any one selected from the group consisting of an alkyl group having 1 to 10 carbon atoms, an alkenyl group having 2 to 10 carbon atoms, an alkynyl group having 2 to 10 carbon atoms, a cycloalkyl group having 3 to 12 carbon atoms, and a cycloalkenyl group having 3 to 12 carbon atoms, $R_1$ and $R_2$ may each independently be any one selected from the group consisting of hydrogen (H), an alkyl group having 1 to 10 carbon atoms, an alkenyl group having 2 to 10 carbon atoms, an alkynyl group having 2 to 10 carbon atoms, a cycloalkyl group having 3 to 12 carbon atoms, and a cycloalkenyl group having 3 to 12 carbon atoms, and A may be an alkylene group having 1 to 5 carbon atoms.

13 Claims, No Drawings

NON-AQUEOUS ELECTROLYTE INCLUDING ADDITIVE FOR NON-AQUEOUS ELECTROLYTE AND LITHIUM SECONDARY BATTERY INCLUDING THE SAME

CROSS-REFERENCE TO RELATED APPLICATIONS

This application is a national stage entry under 35 U.S.C. § 371 of International Application No. PCT/KR2022/014692 filed on Sep. 29, 2022, which claims priority from Korean Patent Application No. 10-2021-0129872, filed on Sep. 30, 2021, all the disclosures of which are incorporated by reference herein.

Technical Field

The present disclosure relates to a non-aqueous electrolyte including an additive for a non-aqueous electrolyte and a lithium secondary battery including the same.

Background Art

Recently, demand for a secondary battery having high stability as well as high capacity and high output is increasing as an application area of lithium secondary batteries is rapidly expanding not only to electricity, electronics, communication, and power supply of electronic devices such as computers, but also to power storage supply of automobiles or large-area devices such as power storage devices.

Particularly, high capacity, high output, and long-term life characteristics are becoming important in lithium secondary batteries for automotive applications. In order to increase capacity of the secondary battery, a nickel-rich positive electrode active material having high energy density but low stability may be used, or the secondary battery may be operated at a high voltage.

However, in a case in which the secondary battery is operated under the above conditions, transition metal ions may be dissolved from a surface of a positive electrode while an electrode surface structure or a film formed on the surface of the positive/negative electrode is degraded due to a side reaction caused by degradation of an electrolyte as charge and discharge proceed. As described above, since the dissolved transition metal ions degrade passivation ability of a solid electrolyte interphase (SEI) while being electro-deposited on the negative electrode, there occurs a problem in that the negative electrode is degraded.

The degradation phenomenon of the secondary battery tends to be accelerated when a potential of the positive electrode is increased or when the battery is exposed to a high temperature.

Also, a so-called swelling phenomenon, in which gas is generated to increase a thickness of the battery if a lithium ion battery is continuously used for a long time or is left standing at a high temperature, occurs, wherein it is known that an amount of the gas generated in this case depends on a state of the SEI.

Thus, in order to solve this problem, research and development on a method capable of reducing the swelling phenomenon of the secondary battery and increasing stability at high temperatures by inhibiting the dissolution of the metal ions from the positive electrode and forming a stable SEI film on the negative electrode are being attempted.

Technical Problem

An aspect of the present invention provides an additive for a non-aqueous electrolyte which may suppress degradation of a positive electrode, may reduce a side reaction between the positive electrode and the electrolyte, and may form a stable solid electrolyte interphase (SEI) film on a negative electrode.

Another aspect of the present invention provides a non-aqueous electrolyte in which stability at high temperature is improved by including the above additive for a non-aqueous electrolyte.

Another aspect of the present invention provides a lithium secondary battery in which overall performance is improved by improving high-temperature cycle characteristics and high-temperature storage characteristics by including the above non-aqueous electrolyte.

Technical Solution

According to an aspect of the present invention, there is provided a non-aqueous electrolyte including an additive for a non-aqueous electrolyte which is represented by Formula 1:

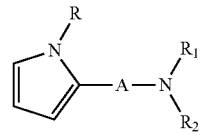

[Formula 1]

wherein, in Formula 1, R is any one selected from the group consisting of an alkyl group having 1 to 10 carbon atoms, an alkenyl group having 2 to 10 carbon atoms, an alkynyl group having 2 to 10 carbon atoms, a cycloalkyl group having 3 to 12 carbon atoms, and a cycloalkenyl group having 3 to 12 carbon atoms, $R_1$ and $R_2$ are each independently any one selected from the group consisting of hydrogen (H), an alkyl group having 1 to 10 carbon atoms, an alkenyl group having 2 to 10 carbon atoms, an alkynyl group having 2 to 10 carbon atoms, a cycloalkyl group having 3 to 12 carbon atoms, and a cycloalkenyl group having 3 to 12 carbon atoms, and A may be an alkylene group having 1 to 5 carbon atoms.

According to another aspect of the present invention, there is provided a lithium secondary battery including the non-aqueous electrolyte.

Advantageous Effects

A compound represented by Formula 1, which is provided as an additive for a non-aqueous electrolyte of the present disclosure, is a compound based on a pyrrole structure in which nitrogen is substituted, wherein it may form a stable SEI (Solid Electrolyte Interphase) film on a surface of a negative electrode while minimizing an increase in resistance of a lithium secondary battery. Thus, the compound represented by Formula 1 may prevent degradation of the negative electrode by suppressing degradation of passivation ability of the SEI at high temperature.

Also, since the compound represented by Formula 1, which is provided as the additive for a non-aqueous electrolyte of the present disclosure, has high binding energy with $PF_5$, which is a charge/discharge by-product of $LiPF_6$ used as a lithium salt, by having a substituent containing an amine group in the pyrrole structure, it has an effect of increasing battery durability by suppressing an additional decomposition reaction of the $PF_5$.

Thus, since an electrode-electrolyte interface, which has low resistance and is stable even at high temperatures, may be formed if the non-aqueous electrolyte of the present disclosure including the compound of Formula 1 is used, a lithium secondary battery, in which overall performance is improved by improving high-temperature cycle characteristics and high-temperature storage characteristics, may be achieved.

DETAILED DESCRIPTION

It will be understood that words or terms used in the specification and claims shall not be interpreted as the meaning defined in commonly used dictionaries. It will be further understood that the words or terms should be interpreted as having a meaning that is consistent with their meaning in the context of the relevant art and the technical idea of the invention, based on the principle that an inventor may properly define the meaning of the words or terms to best explain the invention.

It will be further understood that the terms "include," "comprise," or "have" in this specification specify the presence of stated features, numbers, steps, elements, or combinations thereof, but do not preclude the presence or addition of one or more other features, numbers, steps, elements, or combinations thereof.

Also, the expressions "a" and "b" in the description of "a to b carbon atoms" in the present specification each denote the number of carbon atoms included in a specific functional group. That is, the functional group may include "a" to "b" carbon atoms. For example, the expression "alkylene group having 1 to 5 carbon atoms" denotes an alkylene group including 1 to 5 carbon atoms, such as, —$CH_2$—, —$CH_2CH_2$—, —$CH_2CH_2CH_2$—, —$CH_2CH(CH_3)$—, —$CH(CH_3)$ $CH_2$—, and —$CH(CH_3)$ $CH_2CH_2$—.

Furthermore, in the present specification, the expression "alkylene group" denotes a branched or unbranched divalent hydrocarbon group.

Also, an alkyl group or alkylene group in the present specification may be substituted or unsubstituted. Unless otherwise defined, the expression "substitution" denotes that at least one hydrogen bonded to carbon is substituted with an element other than hydrogen, for example, an alkyl group having 1 to 20 carbon atoms, an alkenyl group having 2 to 20 carbon atoms, an alkynyl group having 2 to 20 carbon atoms, an alkoxy group having 1 to 20 carbon atoms, a cycloalkyl group having 3 to 12 carbon atoms, a cycloalkenyl group having 3 to 12 carbon atoms, a heterocycloalkyl group having 3 to 12 carbon atoms, a heterocycloalkenyl group having 3 to 12 carbon atoms, an aryloxy group having 6 to 12 carbon atoms, a halogen atom, a fluoroalkyl group having 1 to 20 carbon atoms, a nitro group, an aryl group having 6 to 20 carbon atoms, a heteroaryl group having 2 to 20 carbon atoms, or a haloaryl group having 6 to 20 carbon atoms.

Hereinafter, various aspects of the present invention will be described in more detail.

Non-Aqueous Electrolyte

A non-aqueous electrolyte according to an embodiment of the present invention includes a compound represented by Formula 1 below as an additive. A secondary battery including the non-aqueous electrolyte of the present disclosure may have excellent high-temperature cycle characteristics and high-temperature storage characteristics because degradation due to an interfacial reaction at high temperatures is suppressed.

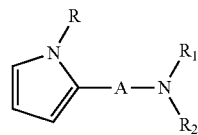

[Formula 1]

The compound of Formula 1 is a compound based on a pyrrole structure in which nitrogen is substituted, wherein it may form a stable SEI (Solid Electrolyte Interphase) film on a surface of a negative electrode while minimizing an increase in resistance of the lithium secondary battery. Thus, it may prevent degradation of the negative electrode by suppressing degradation of passivation ability of the SEI at high temperature. Also, since the compound represented by Formula 1 has high binding energy with $PF_5$, which is a charge/discharge by-product of $LiPF_6$ used as a lithium salt, by having a substituent containing an amine group in the pyrrole structure, it has an effect of increasing battery durability by suppressing an additional decomposition reaction of the $PF_5$.

In Formula 1, R may be any one selected from the group consisting of an alkyl group having 1 to 10 carbon atoms, an alkenyl group having 2 to 10 carbon atoms, an alkynyl group having 2 to 10 carbon atoms, a cycloalkyl group having 3 to 12 carbon atoms, and a cycloalkenyl group having 3 to 12 carbon atoms. Preferably, R of Formula 1 may be a linear or branched alkyl group having 1 to 10 carbon atoms, and most preferably, R of Formula 1 may be a linear alkyl group having 1 to 5 carbon atoms.

In Formula 1, $R_1$ and $R_2$ may each independently be any one selected from the group consisting of hydrogen (H), an alkyl group having 1 to 10 carbon atoms, an alkenyl group having 2 to 10 carbon atoms, an alkynyl group having 2 to 10 carbon atoms, a cycloalkyl group having 3 to 12 carbon atoms, and a cycloalkenyl group having 3 to 12 carbon atoms. Preferably, $R_1$ and $R_2$ of Formula 1 may each independently be any one selected from the group consisting of H and an alkyl group having 1 to 10 carbon atoms. Most preferably, $R_1$ and $R_2$ of Formula 1 may be H.

The compound represented by Formula 1 may be a compound represented by Formula 1-1 below.

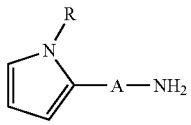

[Formula 1-1]

In Formula 1-1, R may be an alkyl group having 1 to 10 carbon atoms, and A may be an alkylene group having 1 to 5 carbon atoms.

Specifically, the compound represented by Formula 1 may be a compound represented by Formula 1-2 below.

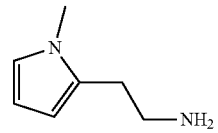

[Formula 1-2]

The additive for a non-aqueous electrolyte according to an embodiment of the present invention may be included in an amount of 0.01 part by weight to 5 parts by weight, preferably 0.05 part by weight to 0.9 part by weight, and more preferably 0.1 part by weight to 0.4 part by weight based on 100 parts by weight of the non-aqueous electrolyte. In a case in which the amount of the compound represented by Formula 1 satisfies the above range, an effect of forming a film on a positive electrode is sufficient to have an effect of inhibiting dissolution of transition metal from a positive electrode active material, and viscosity of the electrolyte is maintained at an appropriate level to have an effect of excellent rate capability or life characteristics during high-temperature storage.

The non-aqueous electrolyte according to an embodiment of the present invention may further include a lithium salt, an organic solvent, or other electrolyte additives.

The lithium salt is used as an electrolyte salt in a lithium secondary battery, wherein it is used as a medium for transferring ions.

The non-aqueous electrolyte according to an embodiment of the present invention may include $LiPF_6$, as the lithium salt, in terms of excellent high-temperature stability. In this case, since the compound represented by Formula 1 has high binding energy with $PF_5$ which is a charge/discharge by-product of the $LiPF_6$ used as the lithium salt, it may have an effect of increasing battery durability by suppressing the additional decomposition reaction of the $PF_5$.

Typically, the lithium salt, for example, may include $Li^+$ as a cation, and may include at least one of $F^-$, $Cl^-$, $Br^-$, $I^-$, $NO_3^-$, $N(CN)_2^-$, $BF_4^-$, $ClO_4^-$, $B_{10}Cl_{10}^-$, $AlCl_4^-$, $AlO_2^-$, $PF_6^-$, $CF_3SO_3^-$, $CH_3CO_2^-$, $CF_3CO_2^-$, $AsF_6^-$, $SbF_6^-$, $CH_3SO_3$, $(CF_3CF_2SO_2)_2N^-$, $(CF_3SO_2)_2N^-$, $(FSO_2)_2N^-$, $BF_2C_2O_4^-$, $BC_4O_8^-$, $PF_4C_2O_4^-$, $PF_2C_4O_8^-$, $(CF_3)_2PF_4^-$, $(CF_3)_3PF_3^-$, $(CF_3)_4PF_2^-$, $(CF_3)_5PF^-$, $(CF_3)_6P^-$, $C_4F_9SO_3^-$, $CF_3CF_2SO_3^-$, $CF_3CF_2$ $(CF_3)_2CO^-$, $(CF_3SO_2)_2CH-$, $CF_3$ $(CF_2)$ $7SO_3^-$, or $SCN^-$ as an anion.

Specifically, the lithium salt may include a single material of LiCl, LiBr, LiI, $LiBF_4$, $LiClO_4$, $LiB_{10}Cl_{10}$, $LiAlCl_4$, $LiAlO_2$, $LiPF_6$, $LiCF_3SO_3$, $LiCH_3CO_2$, $LiCF_3CO_2$, $LiAsF_6$, $LiSbF_6$, $LiCH_3SO_3$, $LiN(SO_2F)2$ (lithium bis(fluorosulfonyl)imide; LiFSI), $LiN(SO_2CF_2CF_3)_2$ (lithium bis(perfluoroethanesulfonyl)imide; LiBETI), or $LiN(SO_2CF_3)_2$ (lithium bis(trifluoromethanesulfonyl)imide; LiTFSI) or a mixture of two or more thereof. In addition to these materials, a lithium salt typically used in an electrolyte of a lithium secondary battery may be used without limitation.

The lithium salt may be appropriately changed in a normally usable range, but may be included in a concentration of 0.5 M to 4 M, preferably 0.5 M to 3 M, and more preferably 0.8 M to 2 M in the electrolyte to obtain an optimum effect of forming a film for preventing corrosion of the surface of the electrode. In a case in which the concentration of the lithium salt satisfies the above range, since an effect of improving cycle characteristics during high-temperature storage of the lithium secondary battery is sufficient and the viscosity of the non-aqueous electrolyte is appropriate, electrolyte impregnability may be improved.

The organic solvent may include at least one of a cyclic carbonate-based organic solvent, a linear carbonate-based organic solvent, a linear ester-based organic solvent, or a cyclic ester-based organic solvent.

Specifically, the organic solvent may include a cyclic carbonate-based organic solvent, a linear carbonate-based organic solvent, or a mixed organic solvent thereof.

The cyclic carbonate-based organic solvent is an organic solvent which may well dissociate the lithium salt in the electrolyte due to high permittivity as a highly viscous organic solvent, wherein specific examples of the cyclic carbonate-based organic solvent may include at least one of ethylene carbonate (EC), propylene carbonate (PC), 1,2-butylene carbonate, 2,3-butylene carbonate, 1,2-pentylene carbonate, 2,3-pentylene carbonate, or vinylene carbonate, and, among them, the cyclic carbonate-based organic solvent may include ethylene carbonate.

Also, the linear carbonate-based organic solvent is an organic solvent having low viscosity and low permittivity, wherein typical examples of the linear carbonate-based organic solvent may include at least one of dimethyl carbonate (DMC), diethyl carbonate (DEC), dipropyl carbonate, ethyl methyl carbonate (EMC), methylpropyl carbonate, or ethylpropyl carbonate, and the linear carbonate-based organic solvent may specifically include ethyl methyl carbonate (EMC).

Furthermore, the organic solvent may further include at least one ester-based organic solvent selected from a linear ester-based organic solvent, or a cyclic ester-based organic solvent in addition to at least one carbonate-based organic solvent selected from the cyclic carbonate-based organic solvent or the linear carbonate-based organic solvent to prepare an electrolyte having high ionic conductivity.

Specific examples of the linear ester-based organic solvent may include at least one of methyl acetate, ethyl acetate, propyl acetate, methyl propionate, ethyl propionate, propyl propionate, or butyl propionate.

Also, the cyclic ester-based organic solvent may include at least one of γ-butyrolactone, γ-valerolactone, γ-caprolactone, σ-valerolactone, or ε-caprolactone.

The organic solvent may be used by adding an organic solvent typically used in a non-aqueous electrolyte without limitation, if necessary. For example, the organic solvent may further include at least one of an ether-based organic solvent, a glyme-based solvent, or a nitrile-based organic solvent.

As the ether-based solvent, any one selected from the group consisting of dimethyl ether, diethyl ether, dipropyl ether, methylethyl ether, methylpropyl ether, ehtylpropyl ether, 1,3-dioxolane (DOL), and 2,2-bis(trifluoromethyl)-1, 3-dioxolane (TFDOL) or a mixture of two or more thereof may be used, but the ether-based solvent is not limited thereto.

The glyme-based solvent is a solvent having higher permittivity and lower surface tension than the linear carbonate-based organic solvent as well as less reactivity with metal, wherein the glyme-based solvent may include at least one of dimethoxyethane (glyme, DME), diethoxyethane, diglyme, tri-glyme (triglyme), or tetra-glyme (TEGDME), but is not limited thereto.

The nitrile-based solvent may include at least one of acetonitrile, propionitrile, butyronitrile, valeronitrile, caprylontrile, heptanenitrile, cyclopentane carbonitrile, cyclohexane carbonitrile, 2-fluorobenzonitrile, 4-fluorobenzonitrile, difluorobenzonitrile, trifluorobenzonitrile, phenylacetonitrile, 2-fluorophenylacetonitrile, or 4-fluorophenylacetonitrile, but is not limited thereto.

Also, the non-aqueous electrolyte of an embodiment of the present invention may further include a known electrolyte additive in the non-aqueous electrolyte, if necessary, in order to prevent the occurrence of collapse of the negative electrode due to decomposition of the non-aqueous electrolyte in a high output environment or to further improve low-temperature high rate discharge characteristics, high-temperature stability, overcharge prevention, and an effect of suppressing battery swelling at high temperature.

Typical examples of the other electrolyte additives may include at least one additive for forming a SEI film which is selected from a cyclic carbonate-based compound, a halogen-substituted carbonate-based compound, a sultone-based compound, a sulfate-based compound, a phosphate-based compound, a borate-based compound, a nitrile-based compound, a benzene-based compound, an amine-based compound, a silane-based compound, or a lithium salt-based compound.

The cyclic carbonate-based compound may include vinylene carbonate (VC) or vinyl ethylene carbonate.

The halogen-substituted carbonate-based compound may include fluoroethylene carbonate (FEC).

The sultone-based compound may include at least one of 1,3-propane sultone (PS), 1,4-butane sultone, ethane sultone, 1,3-propene sultone (PRS), 1,4-butene sultone, or 1-methyl-1,3-propene sultone.

The sulfate-based compound may include ethylene sulfate (Esa), trimethylene sulfate (TMS), or methyl trimethylene sulfate (MTMS).

The phosphate-based compound may include at least one of lithium difluoro (bisoxalato)phosphate, lithium difluorophosphate, tris(trimethyl silyl)phosphate, tris(trimethyl silyl)phosphite, tris(2,2,2-trifluoroethyl)phosphate, or tris (trifluoroethyl)phosphite.

The borate-based compound may include tetraphenylborate, lithium oxalyldifluoroborate (LiODFB), or lithium bis (oxalato)borate (LiB($C_2O_4$)$_2$, LiBOB).

The nitrile-based compound may include at least one of succinonitrile, adiponitrile, acetonitrile, propionitrile, butyronitrile, valeronitrile, caprylonitrile, heptanenitrile, cyclopentane carbonitrile, cyclohexane carbonitrile, 2-fluorobenzonitrile, 4-fluorobenzonitrile, difluorobenzonitrile, trifluorobenzonitrile, phenylacetonitrile, 2-fluorophenylacetonitrile, or 4-fluorophenylacetonitrile.

The benzene-based compound may include fluorobenzene, the amine-based compound may include triethanolamine or ethylenediamine, and the silane-based compound may include tetravinylsilane.

The lithium salt-based compound is a compound different from the lithium salt included in the non-aqueous electrolyte, wherein the lithium salt-based compound may include lithium difluorophosphate (LiDFP), $LiPO_2F_2$, or $LiBF_4$.

In a case in which, among these other electrolyte additives, at least one of vinylene carbonate (VC), 1,3-propane sultone (PS), ethylene sulfate (Esa), or lithium difluorophosphate (LiDFP) is additionally included, a more robust SEI film may be formed on the surface of the negative electrode during an initial activation process of the secondary battery, and high-temperature stability of the secondary battery may be improved by suppressing generation of a gas which may be generated due to the decomposition of the electrolyte at high temperature.

Two or more other electrolyte additives may be mixed and used, and the other electrolyte additives may be included in an amount of 0.050 wt % to 20 wt %, particularly 0.10 wt % to 15 wt %, and preferably 0.30 wt % to 10 wt % based on a total weight of the non-aqueous electrolyte. When the amount of the other electrolyte additives satisfies the above range, an effect of improving ionic conductivity and cycle characteristics is more excellent.

Lithium Secondary Battery

The present invention according to another aspect also provides a lithium secondary battery including the non-aqueous electrolyte.

Specifically, the lithium secondary battery includes a positive electrode including a positive electrode active material, a negative electrode including a negative electrode active material, a separator disposed between the positive electrode and the negative electrode, and the above-described non-aqueous electrolyte.

In this case, the lithium secondary battery of the present disclosure may be prepared according to a typical method known in the art. For example, after an electrode assembly is formed by sequentially stacking a positive electrode, a negative electrode, and a separator between the positive electrode and the negative electrode, the electrode assembly is inserted into a battery case, and the lithium secondary battery may be prepared by injecting the non-aqueous electrolyte according to the present disclosure.

(1) Positive Electrode

The positive electrode may be prepared by coating a positive electrode collector with a positive electrode material mixture slurry including a positive electrode active material, a binder, a conductive agent, and a solvent.

The positive electrode collector is not particularly limited so long as it has conductivity without causing adverse chemical changes in the battery, and, for example, stainless steel, aluminum, nickel, titanium, fired carbon, or aluminum or stainless steel that is surface-treated with one of carbon, nickel, titanium, silver, or the like may be used.

The positive electrode active material is a compound capable of reversibly intercalating and deintercalating lithium, wherein the positive electrode active material may specifically include a lithium metal oxide including lithium and at least one metal such as cobalt, manganese, nickel, or aluminum. More specifically, the lithium metal oxide may include lithium-manganese-based oxide (e.g., $LiMnO_2$, $LiMn_2O_4$, etc.), lithium-cobalt-based oxide (e.g., $LiCoO_2$, etc.), lithium-nickel-based oxide (e.g., $LiNiO_2$, etc.), lithium-nickel-manganese-based oxide (e.g., $LiNi_{1-Y}Mn_YO_2$ (where $0<Y<1$), $LiMn_{2-Z}Ni_ZO_4$ (where $0<Z<2$), etc.), lithium-nickel-cobalt-based oxide (e.g., $LiNi_{1-Y1}Co_{Y1}O_2$ (where $0<Y1<1$), etc.), lithium-manganese-cobalt-based oxide (e.g., $LiCo_{1-Y2}Mn_{Y2}O_2$ (where $0<Y2<1$), $LiMn_{2-Z1}Co_{Z1}O_4$ (where $0<Z1<2$), etc.), lithium-nickel-manganese-cobalt-based oxide (e.g., $Li(Ni_pCo_qMn_r)O_2$ (where $0<p<1$, $0<q<1$, $0<r<1$, and $p+q+r=1$) or $Li(Ni_{p1}Co_{q1}Mn_{r1})O_4$ (where $0<p1<2$, $0<q1<2$, $0<r1<2$, and $p1+q1+r1=2$), etc.), or lithium-nickel-cobalt-transition metal (M) oxide (e.g., $Li(Ni_{p2}Co_{q2}Mn_{r2}M_{S2})O_2$ (where M is selected from the group consisting of aluminum (Al), iron (Fe), vanadium (V), chromium (Cr), titanium (Ti), tantalum (Ta), magnesium (Mg), and molybdenum (Mo), and p2, q2, r2, and s2 are atomic fractions of each independent elements, wherein $0<p2<1$, $0<q2<1$, $0<r2<1$, $0<S2<1$, and $p2+q2+r2+S2=1$), etc.), and any one thereof or a compound of two or more thereof may be included.

Among these materials, in terms of the improvement of capacity characteristics and stability of the battery, the lithium metal oxide may include $LiCoO_2$, $LiMnO_2$, $LiNiO_2$, lithium nickel manganese cobalt oxide (e.g., $Li(Ni_{1/3}Mn_{1/3}Co_{1/3})O_2$, $Li(Ni_{0.6}Mn_{0.2}Co_{0.2})O_2$, $Li(Ni_{0.5}Mn_{0.3}Co_{0.2})O_2$, $Li(Ni_{0.7}Mn_{0.15}Co_{0.15})O_2$, and $Li(Ni_{0.8}Mn_{0.1}Co_{0.1})O_2$, etc.), or lithium nickel cobalt aluminum oxide (e.g., $LiNi_{0.8}Co_{0.15}Al_{0.05}O_2$, etc.), and any one thereof or a mixture of two or more thereof may be used.

Among them, in terms of the fact that the capacity characteristics of the battery may be most improved, a positive electrode active material having a nickel content of 80 atm % or more may be used. For example, the lithium transition metal oxide may include one represented by [Formula 2] below.

$$Li_xNi_aCO_bM^1{}_cM^2{}_dO_2 \qquad \text{[Formula 2]}$$

In Formula 2, $M^1$ is at least one of manganese (Mn) or aluminum (Al), and may be preferably Mn or a combination of Mn and Al.

$M^2$ may be at least one of zirconium (Zr), boron (B), tungsten (W), magnesium (Mg), cerium (Ce), hafnium (Hf), tantalum (Ta), lanthanum (La), titanium (Ti), strontium (Sr), barium (Ba), fluorine (F), phosphorus (P), or sulfur (S).

x represents an atomic fraction of lithium in the lithium transition metal oxide, wherein x may satisfy $0.90 \le x \le 1.1$, may preferably satisfy $0.95 \le x \le 1.08$, and may more preferably satisfy $1.0 \le x \le 1.08$.

a represents an atomic fraction of nickel among metallic elements excluding lithium in the lithium transition metal oxide, wherein a may satisfy $0.80 \le a \le 1.0$, may preferably satisfy $0.80 \le a \le 0.95$, and may more preferably satisfy $0.80 \le a \le 0.90$. In a case in which the amount of the nickel satisfies the above range, high capacity characteristics may be achieved.

b represents an atomic fraction of cobalt among the metallic elements excluding lithium in the lithium transition metal oxide, wherein b may satisfy $0<b<0.2$, $0 \le b\ 0.15$, or $0.01 \le b \le 0.10$.

c represents an atomic fraction of $M^1$ among the metallic elements excluding lithium in the lithium transition metal oxide, wherein c may satisfy $0<c<0.2$, $0<c \le 0.15$, or $0.01 \le c \le 0.10$.

d represents an atomic fraction of $M^2$ among the metallic elements excluding lithium in the lithium transition metal oxide, wherein d may satisfy $0 \le d \le 0.1$ or $0 \le d \le 0.05$.

The positive electrode active material may be included in an amount of 60 wt % to 99 wt %, preferably 70 wt % to 99 wt %, and more preferably 80 wt % to 98 wt % based on a total weight of a solid content excluding the solvent in the positive electrode material mixture slurry.

The binder is a component that assists in the binding between the active material and the conductive agent and in the binding with the current collector.

Examples of the binder may be polyvinylidene fluoride, polyvinyl alcohol, starch, hydroxypropylcellulose, regenerated cellulose, polyvinylpyrrolidone, polytetrafluoroethylene, polyethylene (PE), polypropylene, an ethylene-propylene-diene monomer, a sulfonated ethylene-propylene-diene monomer, a styrene-butadiene rubber, a fluoro rubber, or various copolymers.

The binder may commonly be included in an amount of 1 wt % to 20 wt %, preferably 1 wt % to 15 wt %, and more preferably 1 wt % to 10 wt % based on the total weight of the solid content excluding the solvent in the positive electrode material mixture slurry.

The conductive agent is a component for further improving conductivity of the positive electrode active material, wherein it may be added in an amount of 1 wt % to 20 wt % based on the total weight of the solid content in the positive electrode material mixture slurry. The conductive agent is not particularly limited as long as it has conductivity without causing adverse chemical changes in the battery, and, for example, a conductive material, such as: carbon powder such as carbon black, acetylene black, Ketjen black, channel black, furnace black, lamp black, or thermal black; graphite powder such as natural graphite with a well-developed crystal structure, artificial graphite, or graphite; conductive fibers such as carbon fibers or metal fibers; fluorocarbon powder; conductive powder such as aluminum powder or nickel powder; conductive whiskers such as zinc oxide whiskers or potassium titanate whiskers; conductive metal oxide such as titanium oxide; or polyphenylene derivatives, may be used.

The conductive agent may commonly be included in an amount of 1 wt % to 20 wt %, preferably 1 wt % to 15 wt %, and more preferably 1 wt % to 10 wt % based on the total weight of the solid content excluding the solvent in the positive electrode material mixture slurry.

The solvent may include an organic solvent, such as N-methyl-2-pyrrolidone (NMP), and may be used in an amount such that desirable viscosity is obtained when the positive electrode active material as well as optionally the binder and the conductive agent is included. For example, the solvent may be included in an amount such that a concentration of the solid content including the positive electrode active material as well as optionally the binder and the conductive agent is in a range of 50 wt % to 95 wt %, preferably 70 wt % to 95 wt %, and more preferably 70 wt % to 90 wt %.

(2) Negative Electrode

The negative electrode, for example, may be prepared by coating a negative electrode material mixture slurry including a negative electrode active material, a binder, a conductive agent, and a solvent on a negative electrode collector, or a graphite electrode formed of carbon (C) or a metal itself may be used as the negative electrode.

For example, in a case in which the negative electrode is prepared by coating the negative electrode material mixture slurry on the negative electrode collector, the negative electrode collector generally has a thickness of 3 µm to 500 µm. The negative electrode collector is not particularly limited so long as it has high conductivity without causing adverse chemical changes in the battery, and, for example, copper, stainless steel, aluminum, nickel, titanium, fired carbon, copper or stainless steel that is surface-treated with one of carbon, nickel, titanium, silver, or the like, an aluminum-cadmium alloy, or the like may be used. Also, similar to the positive electrode collector, the negative electrode collector may have fine surface roughness to improve bonding strength with the negative electrode active material, and the negative electrode collector may be used in various shapes such as a film, a sheet, a foil, a net, a porous body, a foam body, a non-woven fabric body, and the like.

Also, the negative electrode active material may include at least one of lithium metal, a carbon material capable of reversibly intercalating/deintercalating lithium ions, metal or an alloy of lithium and the metal, a metal composite oxide, a material which may be doped and undoped with lithium, or a transition metal oxide.

As the carbon material capable of reversibly intercalating/deintercalating lithium ions, a carbon-based negative electrode active material generally used in a lithium ion secondary battery may be used without particular limitation, and, as a typical example, crystalline carbon, amorphous carbon, or both thereof may be used. Examples of the crystalline carbon may be graphite such as irregular, planar, flaky, spherical, or fibrous natural graphite or artificial graphite, and examples of the amorphous carbon may be soft carbon (low-temperature sintered carbon) or hard carbon, mesophase pitch carbide, or fired cokes.

One selected from the group consisting of PbO, $PbO_2$, $Pb_2O_3$, $Pb_3O_4$, $Sb_2O_3$, $Sb_2O_4$, $Sb_2O_5$, GeO, $GeO_2$, $Bi_2O_3$, $Bi_2O_4$, $Bi_2O_5$, $Li_xFe_2O_3$ ($0 \le x \le 1$), $Li_xWO_2$ ($0 \le x \le 1$), and $Sn_xMe_{1-x}Me'_yO_z$ (Me: Mn, Fe, lead (Pb), or germanium (Ge); Me': Al, B, P, silicon (Si), Groups I, II and III elements of the periodic table, or halogen; 0<x≤1; 1≤y≤3; 1≤z≤8) may be used as the metal composite oxide.

The material, which may be doped and undoped with lithium, may include Si, $SiO_x$ (0<x≤2), a Si—Y alloy (where Y is an element selected from the group consisting of alkali metal, alkaline earth metal, a Group 13 element, a Group 14 element, transition metal, a rare earth element, and a combination thereof, and is not Si), tin (Sn), $SnO_2$, or Sn—Y (where Y is an element selected from the group consisting of alkali metal, alkaline earth metal, a Group 13 element, a Group 14 element, transition metal, a rare earth element, and a combination thereof, and is not Sn), or a mixture of $SiO_2$ and at least one thereof may also be used. The element Y may be selected from the group consisting of Mg, calcium (Ca), Sr, Ba, radium (Ra), scandium (Sc), yttrium (Y), Ti, Zr, Hf, rutherfordium (Rf), V, niobium (Nb), Ta, dubnium (db), Cr, Mo, W, seaborgium (Sg), technetium (Tc), rhenium (Re), bohrium (Bh), Fe, Pb, ruthenium (Ru), osmium (Os), hassium (Hs), rhodium (Rh), iridium (Ir), palladium (Pd), platinum (Pt), copper (Cu), silver (Ag), gold (Au), zinc (Zn), cadmium (Cd), B, Al, gallium (Ga), Sn, indium (In), Ge, P, arsenic (As), antimony (Sb), bismuth (Bi), S, selenium (Se), tellurium (Te), polonium (Po), and a combination thereof.

The transition metal oxide may include lithium-containing titanium composite oxide (LTO), vanadium oxide, or lithium vanadium oxide.

The negative electrode active material may be included in an amount of 60 wt % to 99 wt %, preferably 70 wt % to 99 wt %, and more preferably 80 wt % to 98 wt % based on a total weight of solid content in the negative electrode material mixture slurry.

Examples of the binder may be polyvinylidene fluoride (PVDF), polyvinyl alcohol, starch, hydroxypropylcellulose, regenerated cellulose, polyvinylpyrrolidone, polytetrafluoroethylene, polyethylene, polypropylene, an ethylene-propylene-diene monomer, a sulfonated ethylene-propylene-diene monomer, a styrene-butadiene rubber, a fluoro rubber, or various copolymers thereof. Specifically, styrene-butadiene rubber (SBR)-carboxymethyl cellulose (CMC) may be used in terms of high thickening.

The binder may be commonly included in an amount of 1 wt % to 20 wt %, preferably 1 wt % to 15 wt %, and more preferably 1 wt % to 10 wt % based on the total weight of the solid content excluding the solvent in the negative electrode material mixture slurry.

The conductive agent is a component for further improving conductivity of the negative electrode active material, wherein the conductive agent may be added in an amount of 1 wt % to 20 wt % based on the total weight of the solid content in the negative electrode slurry. The conductive agent is not particularly limited as long as it has conductivity without causing adverse chemical changes in the battery, and, for example, a conductive material, such as: carbon powder such as carbon black, acetylene black, Ketjen black, channel black, furnace black, lamp black, or thermal black; graphite powder such as natural graphite with a well-developed crystal structure, artificial graphite, or graphite; conductive fibers such as carbon fibers or metal fibers; fluorocarbon powder; conductive powder such as aluminum powder or nickel powder; conductive whiskers such as zinc oxide whiskers or potassium titanate whiskers; conductive metal oxide such as titanium oxide; or polyphenylene derivatives, may be used.

The conductive agent may be included in an amount of 1 wt % to 20 wt %, preferably 1 wt % to 15 wt %, and more preferably 1 wt % to 10 wt % based on the total weight of the solid content excluding the solvent in the negative electrode material mixture slurry.

The solvent may include water or an organic solvent, such as NMP (N-methyl-2-pyrrolidone), and may be used in an amount such that desirable viscosity is obtained when the negative electrode active material as well as optionally the binder and the conductive agent is included. For example, the solvent may be included in an amount such that a concentration of the solid content including the negative electrode active material as well as optionally the binder and the conductive agent is in a range of 50 wt % to 95 wt %, preferably, 70 wt % to 90 wt %.

In a case in which the metal itself is used as the negative electrode, the negative electrode may be a metal thin film itself or may be prepared by a method in which the metal is physically bonded, rolled, or deposited on the negative electrode collector. As the deposition method, an electrical deposition method or a chemical vapor deposition method for the metal may be used.

For example, the metal thin film itself or the metal to be bonded/rolled/deposited on the negative electrode collector may include one type of metal selected from lithium (Li), nickel (Ni), tin (Sn), copper (Cu), or indium (In) or an alloy of two types of metals.

(3) Separator

Also, a conventional porous polymer film typically used as a separator, for example, a porous polymer film prepared from a polyolefin-based polymer, such as an ethylene homopolymer, a propylene homopolymer, an ethylene/butene copolymer, an ethylene/hexene copolymer, or an ethylene/methacrylate copolymer, may be used alone or in a lamination therewith as the separator, and a typical porous nonwoven fabric, for example, a nonwoven fabric formed of high melting point glass fibers or polyethylene terephthalate fibers may be used, but the present invention is not limited thereto. Furthermore, a coated separator including a ceramic component or a polymer material may be used to secure heat resistance or mechanical strength, and the separator having a single layer or multilayer structure may be optionally used.

Specifically, a safety reinforced separator (SRS), in which a coating layer containing a ceramic component or a polymer material is formed to secure heat resistance or mechanical strength, may be used as the separators included in the electrode assembly of the present disclosure.

Specifically, the separators included in the electrode assembly of the present disclosure include a porous separator support and a porous coating layer entirely coated on one or both surfaces of the separator support, wherein the coating layer may include a mixture of inorganic particles, which are selected from metal oxide, metalloid oxide, metal fluoride, metal hydroxide, or a combination thereof, and a binder polymer that connects and fixes the inorganic particles to each other.

The coating layer may include at least one of $Al_2O_3$, $SiO_2$, $TiO_2$, $SnO_2$, $CeO_2$, MgO, NiO, CaO, ZnO, $ZrO_2$, $Y_2O_3$, $SrTiO_3$, $BaTiO_3$, $Mg(OH)_2$, or MgF, as the inorganic particles. Herein, the inorganic particles may improve thermal stability of the separator. That is, the inorganic particles may prevent the separator from shrinking at high temperatures. In addition, the binder polymer may improve mechanical stability of the separator by fixing the inorganic particles.

A shape of the lithium secondary battery of the present disclosure is not particularly limited, but a cylindrical type using a can, a prismatic type, a pouch type, or a coin type may be used.

Hereinafter, the present invention will be described in detail, according to specific examples. However, the following examples are merely presented to exemplify the present invention, and the scope of the present invention is not limited thereto. It will be apparent to those skilled in the art that various modifications and alterations are possible within the scope and technical spirit of the present invention, and such modifications and alterations fall within the scope of claims included herein.

EXAMPLES

Example 1

Preparation of Non-Aqueous Electrolyte

A non-aqueous solvent was prepared by dissolving $LiPF_6$ and vinylene carbonate (VC) in an organic solvent (ethylene carbonate (EC):ethyl methyl carbonate (EMC)=30:70 volume ratio) such that amounts thereof were 1.0 M and 0.5 wt %, respectively, and a non-aqueous electrolyte was prepared by adding 0.1 g of the compound of Formula 1-2 to 99.9 g of the non-aqueous solvent.

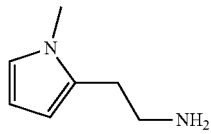

[Formula 1-2]

Lithium Secondary Battery Preparation

A positive electrode active material ($LiNi_{0.9}Co_{0.06}Mn_{0.03}Al_{0.01}O_2$):a conductive agent (carbon black):a binder (polyvinylidene fluoride) were added in a weight ratio of 97.6:0.8:1.6 to N-methyl-2-pyrrolidone (NMP), as a solvent, to prepare a positive electrode slurry (solid content 60 wt %). One surface of a 13.5 μm thick positive electrode collector (Al thin film) was coated with the positive electrode slurry, dried, and roll-pressed to prepare a positive electrode.

A negative electrode active material (graphite:SiO=90.0: 10.0 weight ratio):a conductive agent (carbon black):a binder (styrene-butadiene rubber (SBR)-carboxymethyl cellulose (CMC)) were added to N-methyl-2-pyrrolidone (NMP), as a solvent, in a weight ratio of 97.6:0.8:1.6 to prepare a negative electrode slurry (solid content 60 wt %). One surface of a 6 μm thick negative electrode collector (Cu thin film) was coated with the negative electrode slurry, dried, and roll-pressed to prepare a negative electrode.

After disposing a polyolefin-based porous separator coated with $Al_2O_3$ inorganic particles between the above-prepared positive electrode and negative electrode in a dry room, a secondary battery was prepared by injecting the above-prepared non-aqueous electrolyte.

Example 2

A secondary battery was prepared in the same manner as in Example 1 except that a non-aqueous electrolyte was prepared by adding 0.3 g of the compound of Formula 1-2 to 99.7 g of the non-aqueous solvent prepared in Example 1.

Example 3

A secondary battery was prepared in the same manner as in Example 1 except that a non-aqueous electrolyte was prepared by adding 0.5 g of the compound of Formula 1-2 to 99.5 g of the non-aqueous solvent prepared in Example 1.

Comparative Example 1

A secondary battery was prepared in the same manner as in Example 1 except that a non-aqueous electrolyte was prepared by using 100 g of the non-aqueous solvent prepared in Example 1.

Comparative Example 2

A secondary battery was prepared in the same manner as in Example 1 except that a non-aqueous electrolyte was prepared by adding 0.1 g of a compound of Formula A below to 99.9 g of the non-aqueous solvent prepared in Example 1.

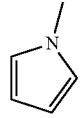

[Formula A]

Experimental Example 1—High-Temperature Cycle Characteristics Evaluation

Cycle characteristics were evaluated for each of the secondary batteries prepared in Examples 1 to 3 and Comparative Examples 1 and 2.

Specifically, after charging of each of the batteries prepared in Examples 1 to 3 and Comparative Examples 1 and 2 at a constant current of 0.33 C to 4.2 V at 45° C. and discharging of each battery at a constant current of 0.33 C to 2.8 V were set as one cycle and 100 cycles of the charging and discharging were performed, capacity retention relative to initial capacity after 100 cycles was measured. The results thereof are presented in Table 1 below.

TABLE 1

| | Capacity retention (%) |
|---|---|
| Example 1 | 95.9 |
| Example 2 | 96.2 |
| Example 3 | 95.8 |
| Comparative Example 1 | 95.4 |
| Comparative Example 2 | 95.3 |

As illustrated in Table 1, since Examples 1 to 3 using the additive for a non-aqueous electrolyte of the present disclosure had higher capacity retentions than Comparative Examples 1 and 2 in which the additive was not used, their life characteristics were excellent.

Experimental Example 2—High-Temperature Storage Characteristics Evaluation

High-temperature storage characteristics were evaluated for each of the secondary batteries prepared in Examples 1 to 3 and Comparative Examples 1 and 2.

Specifically, after fully charging of each of the secondary batteries prepared in Examples 1 to 3 and Comparative Examples 1 and 2 to 4.2 V, each secondary battery was stored at 60° C. for 4 weeks.

Before the storage, resistance of the fully charged secondary battery was measured to set it as initial resistance of the secondary battery.

After 4 weeks, resistance of the stored secondary battery was measured to calculate resistance that had been increased during a storage period of 4 weeks. A percent ratio of the increased resistance to the initial resistance of the secondary battery was calculated to derive a resistance increase rate after 4 weeks. The results thereof are presented in Table 2 below.

TABLE 2

|  | Resistance increase rate (%) |
|---|---|
| Example 1 | 8.87 |
| Example 2 | 8.29 |
| Example 3 | 8.59 |
| Comparative Example 1 | 9.25 |
| Comparative Example 2 | 9.15 |

As illustrated in Table 2, it was confirmed that the secondary batteries of Examples 1 to 3 had stable performance at high temperature because their resistance increase rates after 4 weeks were smaller than those of the secondary batteries of Comparative Examples 1 and 2.

The invention claimed is:

1. A non-aqueous electrolyte comprising an additive represented by Formula 1:

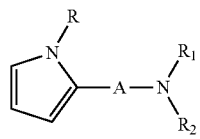

[Formula 1]

wherein in Formula 1, R is any one selected from the group consisting of an alkyl group having 1 to 10 carbon atoms, an alkenyl group having 2 to 10 carbon atoms, an alkynyl group having 2 to 10 carbon atoms, a cycloalkyl group having 3 to 12 carbon atoms, and a cycloalkenyl group having 3 to 12 carbon atoms, $R_1$ and $R_2$ are each independently any one selected from the group consisting of hydrogen (H), an alkyl group having 1 to 10 carbon atoms, an alkenyl group having 2 to 10 carbon atoms, an alkynyl group having 2 to 10 carbon atoms, a cycloalkyl group having 3 to 12 carbon atoms, and a cycloalkenyl group having 3 to 12 carbon atoms, and A is an alkylene group having 1 to 5 carbon atoms.

2. The non-aqueous electrolyte of claim 1, wherein $R_1$ and $R_2$ in Formula 1 are H.

3. The non-aqueous electrolyte of claim 1, wherein R in Formula 1 is an alkyl group having 1 to 10 carbon atoms.

4. The non-aqueous electrolyte of claim 1, wherein the additive represented by Formula 1 is a compound represented by Formula 1-1:

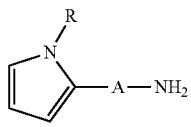

[Formula 1-1]

wherein; in Formula 1-1, R is an alkyl group having 1 to 10 carbon atoms, and

A is an alkylene group having 1 to 5 carbon atoms.

5. The non-aqueous electrolyte of claim 1, wherein the additive represented by Formula 1 is a compound represented by Formula 1-2

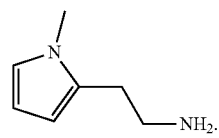

[Formula 1-2]

6. The non-aqueous electrolyte of claim 1, wherein the additive is included in an amount of 0.01 part by weight to 5 parts by weight based on 100 parts by weight of the non-aqueous electrolyte.

7. The non-aqueous electrolyte of claim 1, further comprising $LiPF_6$ as a lithium salt.

8. The non-aqueous electrolyte of claim 7, wherein the $LiPF_6$ is included in a concentration of 0.5 M to 4 M.

9. The non-aqueous electrolyte of claim 7, further comprising at least a second lithium salt selected from LiCl, LiBr, LiI, $LiBF_4$, $LiClO_4$, $LiB_{10}Cl_{10}$, $LiAlCl_4$, $LiAlO_2$, $LiCF_3SO_3$, $LiCH_3CO_2$, $LiCF_3CO_2$, $LiAsF_6$, $LiSbF_6$, $LiCH_3SO_3$, $LiN(SO_2F)_2$, $LiN(SO_2CF_2CF_3)_2$, or $LiN(SO_2CF_3)_2$.

10. The non-aqueous electrolyte of claim 1, further comprising an organic solvent.

11. The non-aqueous electrolyte of claim 10, wherein the organic solvent comprises at least one of a cyclic carbonate-based organic solvent, a linear carbonate-based organic solvent, a linear ester-based organic solvent, or a cyclic ester-based organic solvent.

12. The non-aqueous electrolyte of claim 1, further comprising at least one of a cyclic carbonate-based compound, a halogen-substituted carbonate-based compound, a sultone-based compound, a sulfate-based compound, a phosphate-based compound, a borate-based compound, a nitrile-based compound, a benzene-based compound, an amine-based compound, a silane-based compound, or a lithium salt-based compound, as a second additive.

13. A lithium secondary battery comprising a positive electrode including a positive electrode active material, a negative electrode including a negative electrode active material, a separator disposed between the positive electrode and the negative electrode, and the non-aqueous electrolyte of claim 1.

* * * * *